United States Patent
Vanderwolk

(10) Patent No.: US 9,962,281 B2
(45) Date of Patent: May 8, 2018

(54) PENIS ENHANCEMENT APPARATUS

(71) Applicant: Philip Vanderwolk, Santa Fe, NM (US)

(72) Inventor: Philip Vanderwolk, Santa Fe, NM (US)

( * ) Notice: Subject to any disclaimer, the term of this patent is extended or adjusted under 35 U.S.C. 154(b) by 282 days.

(21) Appl. No.: 14/843,466

(22) Filed: Sep. 2, 2015

(65) Prior Publication Data
US 2016/0058603 A1    Mar. 3, 2016

Related U.S. Application Data

(60) Provisional application No. 62/045,113, filed on Sep. 3, 2014.

(51) Int. Cl.
*A61F 5/41* (2006.01)

(52) U.S. Cl.
CPC .......... *A61F 5/41* (2013.01); *A61F 2005/414* (2013.01)

(58) Field of Classification Search
CPC .............................. A61F 5/41; A61F 2005/414
USPC ...................................... 600/38–41
See application file for complete search history.

(56) References Cited

U.S. PATENT DOCUMENTS

| | | | | |
|---|---|---|---|---|
| 3,930,506 A * | 1/1976 | Overend | ............ | A61B 17/1322 606/203 |
| 4,203,432 A | 5/1980 | Koch | | |
| 4,569,108 A * | 2/1986 | Schwab | ............ | B62J 7/08 24/17 AP |
| 5,027,800 A * | 7/1991 | Rowland | ............ | A61F 5/41 600/39 |
| 5,855,548 A | 1/1999 | Place | | |
| 6,319,194 B1 * | 11/2001 | Wulf | ............ | A61F 5/41 600/41 |
| 7,390,297 B2 | 6/2008 | Ford | | |
| 7,674,225 B2 | 3/2010 | Shelyakov et al. | | |
| 7,678,042 B2 * | 3/2010 | Jackson | ............ | A61F 5/41 600/41 |
| 8,162,819 B2 | 4/2012 | Adams | | |
| 2004/0152948 A1 * | 8/2004 | Kim | ............ | A61F 5/41 600/38 |
| 2014/0224263 A1 * | 8/2014 | Wilson | ............ | A24F 3/00 131/186 |

* cited by examiner

*Primary Examiner* — John Lacyk
(74) *Attorney, Agent, or Firm* — Global Intellectual Property Agency, LLC; Daniel Enea

(57) ABSTRACT

A penis enhancement apparatus and method having a first ring and a second ring, wherein each ring is circular in shape having an opening for receiving a penis therethough. The method provides the steps of adjusting the rings to an appropriate size via securing a knot in each ring. The first ring is applied to the tip of the penis adjacent to the glans thereof. The second ring is placed onto the shaft of the penis near the scrotum, wherein the rings cause small tears in the tissue of the penis via putting pressure onto the tissue of the penis once applied thereto. Pressure is then manually applied to the scrotum in order to direct blood flow into the tissue of the penis, wherein the blood causes the small tears. As the small tears are repaired, the penis is enlarged due to the promotion of cell growth and cell division.

1 Claim, 3 Drawing Sheets

PENIS ENHANCEMENT APPARATUS

CROSS REFERENCE TO RELATED APPLICATION

This application claims the benefit of U.S. Provisional Application No. 62/045,113 filed on Sep. 3, 2014. The above identified patent application is herein incorporated by reference in its entirety to provide continuity of disclosure.

BACKGROUND OF THE INVENTION

Field of the Invention

The present invention relates to a penis enhancement apparatus that can be utilized to enlarge, extend and overall enhance the size and girth of one's penis. The device comprises a pair of rings configured to be positioned around opposing ends of a user's penis in order to increase and/or isolate the blood flow and promote cell growth therebetween.

It is embarrassing and uncomfortable for most men when engaging in intimate acts with another if one does not feel confident with the size, appearance, or girth of one's penis. Some men may resort to taking various drugs in order to enlarge one's penis. This may result in harmful and dangerous side effects to the user. Other men may use various contraptions and devices in order to increase the size of one's penis, however this can result in injury to the penis and damage to the internal vessels thereof. Thus, there exists a need in the prior art for an apparatus that safely and conveniently enlarges the size of one's penis.

Devices have been disclosed in the prior art that relate to penis enhancement apparatuses. These include devices that have been patented and published in patent application publications. These devices generally relate to penis extension or enlargement apparatuses having various methods and configurations for attachment to and enhancement of the penis. The following is a list of devices deemed most relevant to the present disclosure, which are herein described for the purposes of highlighting and differentiating the unique aspects of the present invention, and further highlighting the drawbacks existing in the prior art.

Some devices comprise penis enlargement apparatuses that are cumbersome and uncomfortable, wherein these devices are adapted to attach to the penis on one end thereof and a body member, such as the user's neck, on the other end thereof. As such, these devices employ a mechanical stretching technique in order to increase the length of one's penis. This technique, however, is ineffective, dangerous and can result in injuries to the user's penis and other body parts.

Other devices involve the use of compression elements for placement around the shaft of a penis in order to maintain the erection thereof during sexual intercourse. This however, is not helpful in the way of enlarging the girth and length of a penis, but rather acts to memorize the shape of the user's erect penis such that it adjusts accordingly for the user during intercourse for prolonging an erection.

These prior art devices have several known drawbacks. The above discussed devices are ineffective in enhancing the length and girth of one's penis. Further, the above mentioned devices do not provide a method of use that involves creating small tears in the blood vessels and tissue of the penis in order to promote the physiological process of cell growth which is known as hypertrophy and cell division which is known as hyperplasia.

It is submitted that the present invention substantially diverges in design elements from the prior art and consequently it is clear that there is a need in the art for an improvement to existing penis enhancement apparatuses. In this regard the instant invention substantially fulfills these needs.

SUMMARY OF THE INVENTION

In view of the foregoing disadvantages inherent in the known types of penis enhancement apparatuses now present in the prior art, the present invention provides a new penis enhancement apparatus wherein the same can be utilized for providing convenience for enlarging one's penis.

It is therefore an object of the present invention to provide a new and improved penis enhancement apparatus that has all of the advantages of the prior art and none of the disadvantages.

It is another object of the present invention to provide a penis enhancement apparatus that can be utilized before engaging in sexual activity.

Another object of the present invention is to provide a penis enhancement apparatus comprising a pair of rings, wherein each ring is adjustable in diameter so as to accommodate the penis size of the user.

Yet another object of the present invention is to provide a penis enhancement apparatus having a method of use intended to promote the physiological process of cell growth or hypertrophy and cell division known as hyperplasia in order to enlarge the girth and length of the penis.

Another object of the present invention is to provide a penis enhancement apparatus having a method of use that stimulates cell growth in the penis of the user.

Another object of the present invention is to provide a penis enhancement apparatus that is flexible.

Another object of the present invention is to provide a penis enhancement apparatus having fasteners in an alternative embodiment.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1A:
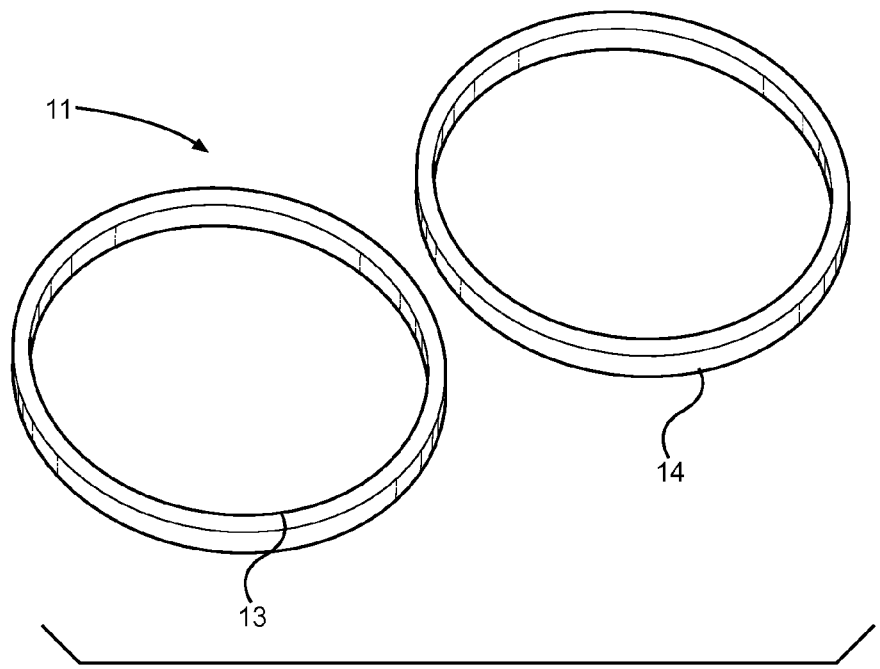
FIG. 1a shows a view of the first and second ring of the penis enhancement apparatus.

Reference is made herein to the attached drawings. Like reference numerals are used throughout the drawings to depict like or similar elements of the penis enhancement apparatus. For the purposes of presenting a brief and clear description of the present invention, the preferred embodiment will be discussed as used for causing small tears or micro-tears in blood vessels and the tissue of the penis in order to promote new cell growth therein, thus increasing the size of one's penis. The figures are intended for representative purposes only and should not be considered to be limiting in any respect.

Referring now to FIG. 1a, there is shown a view of the first ring and the second ring of the penis enhancement apparatus 11 of the present invention and the method in which it is to be used. The penis enhancement apparatus 11 comprises a first ring 13 and a second ring 14, wherein each ring 13, 14 comprises a flexible band that is planar in structure. The penis enhancement apparatus 11 is configured to be disposed on a human penis having a tip 12 and a base, wherein the tip 12 of the penis comprises the glans, wherein the glans extends into the shaft 25 of the penis and the base. Further, the base of the shaft 25 extends into the scrotum 15.

The rings 13, 14 are circular in shape and comprise an opening for receiving a penis therethrough. Each ring 13, 14, is configured to be placed onto the shaft 25 of the penis, wherein the rings 13, 14 lay flush against the shaft, thereby encircling the width thereof. Each ring 13, 14 further comprises a unitary structure. It should be noted that the penis contains various types of tissue, being the corpus cavernosum and the corpus spongiosum. The corpus cavernosum consists of two columns of tissue that extend along the sides of the penis, wherein blood fills this tissue in order to cause an erection. The corpus spongiosum consists of a column of sponge-like tissue that extending from the base of the penis through the glans of the penis. The rings 13, 14 can be composed of rubber, cotton, nylon, neoprene, plastic, latex or other suitable materials.

Figure 1B:
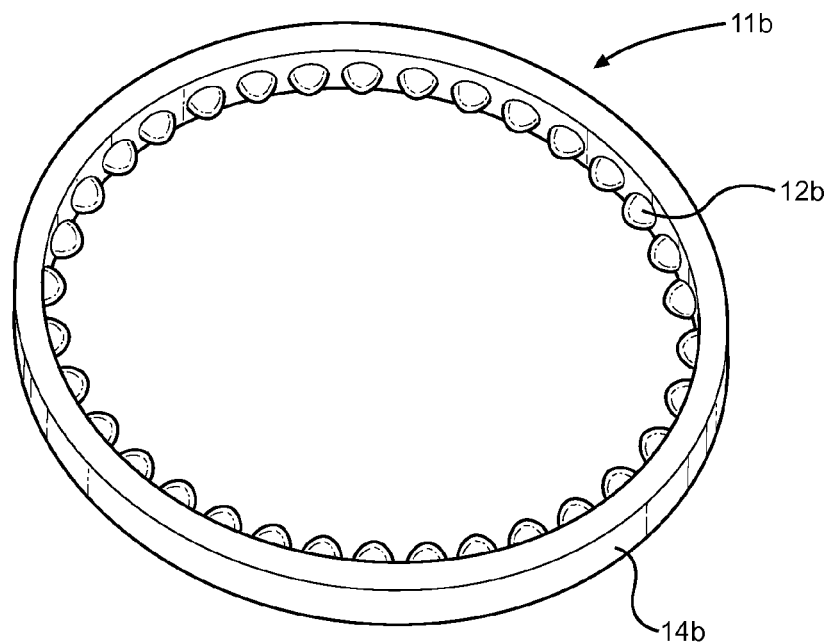
FIG. 1b shows a view of an alternative embodiment of the first and second ring of the penis enhancement apparatus.

Referring now to FIG. 1b, there is shown an alternative structure of at least one of the rings 14b of the penis enhancement apparatus 11b. In an alternative embodiment, at least one of the rings 14b can comprise a circular shape having an opening, wherein one of the rings 14b or both of the rings provide a planar structure having a first side and a second side. The second side of one of the rings 14b comprises a plurality of small protrusions 12b configured to be disposed against the penis. Upon application of the ring 14b to the penis, the plurality of protrusions 12b heighten the pressure applied to the tissue of the shaft of the penis, thus contributing to the production of small tears in the tissue of the penis. The second side of each of the rings 14b when placed upon the shaft of the penis create pressure applied thereto and result in small tears therein. Further, in an alternative embodiment, at least one of the rings 14b can provide fasteners integral therewith in order to allow for the adjustability thereof.

Figure 2:
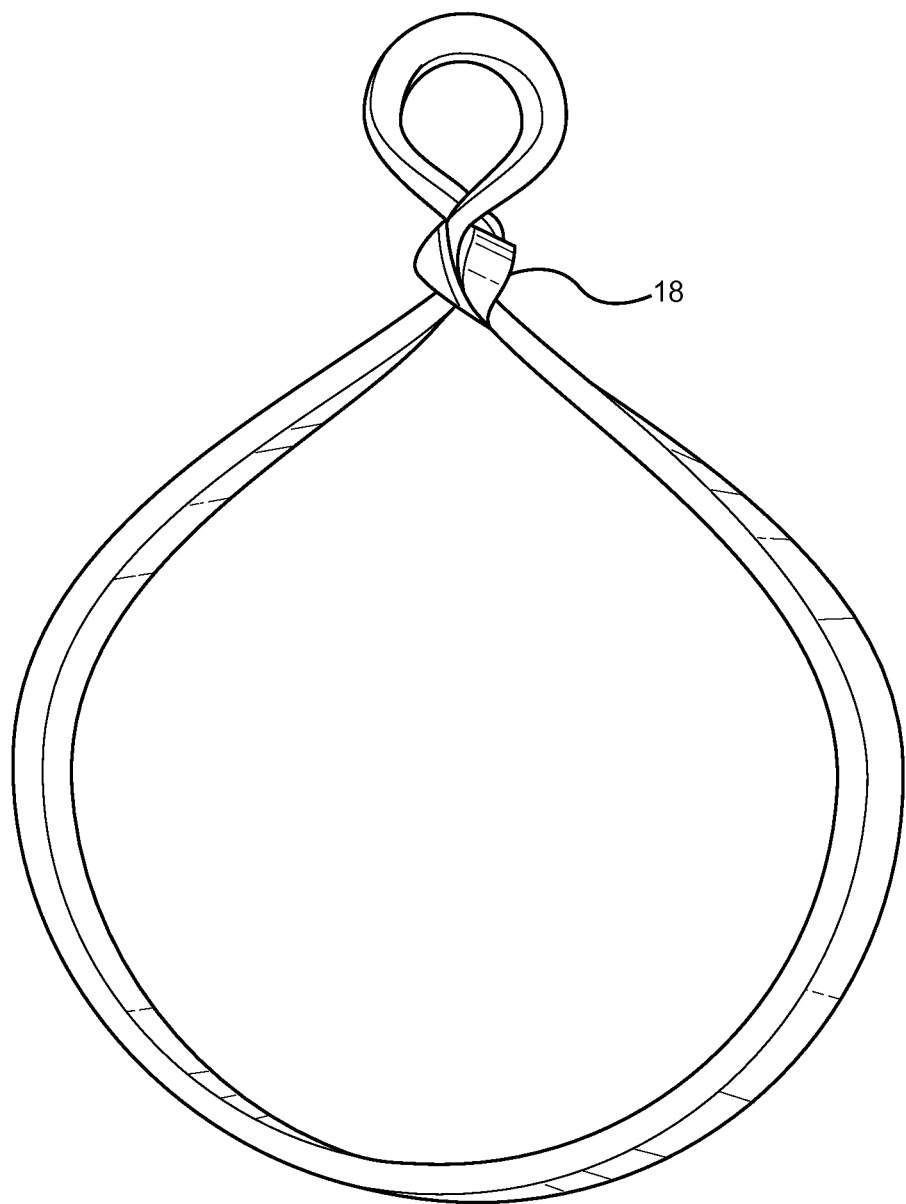
FIG. 2 shows a view of the way in which the first and second ring is knotted of the penis enhancement apparatus.
Figure 3:
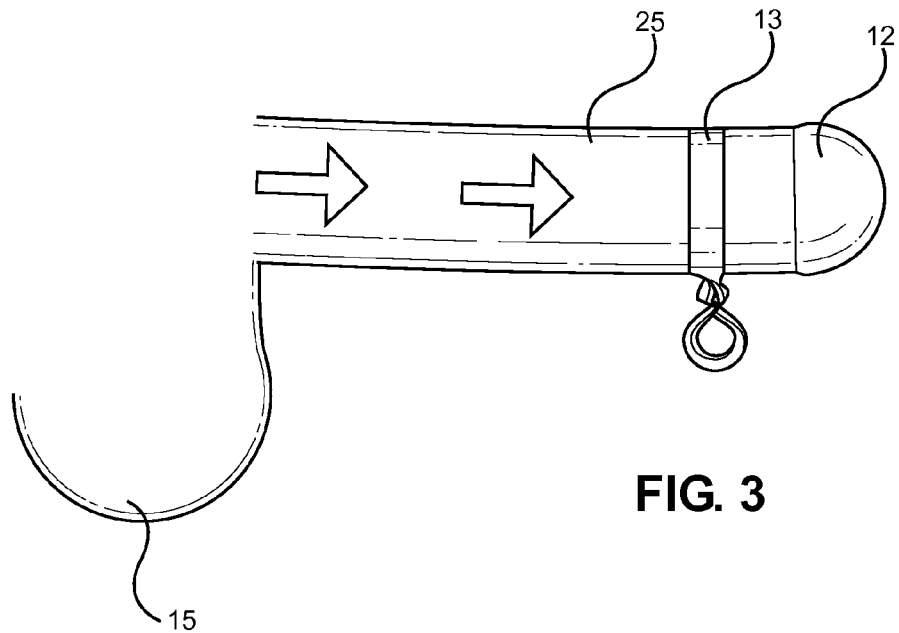
FIG. 3 shows a view of the first ring applied to the penis.
Figure 4:
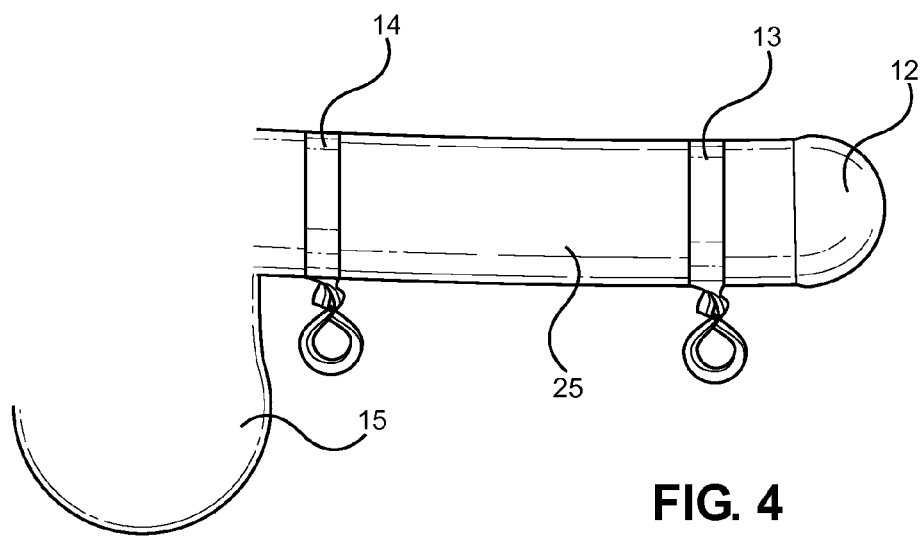
FIG. 4 shows a view of the first ring and the second ring applied to the penis.

Referring now to FIGS. 2, 3 and 4, there is shown the way in which the first ring 13 and second ring 14 can be placed into a knot 18 and there is shown the first ring 13 applied to a penis and the first ring 13 and the second ring 14 applied to a penis. Before use, the user can adjust the size of the first ring 13 and the second ring 14 in order to provide a desired diameter to fit the size of the penis of the user so as to allow pressure to be exerted thereon. The penis should preferentially be semi-erect when using the penis enhancement apparatus 11. In the illustrated embodiment, a knot 18 is tied into each ring so as to adjust the diameter thereof. Then, the user can proceed to place the first ring 13 adjacent to the tip 12 of the penis on the shaft 25, below the glans thereof. Once the first ring 13 is placed below the glans, the first ring 13 causes physical pressure to be exerted onto the shaft 25 of the penis, thus applying stress to the tissue and blood vessels of the penis. The external physical pressure and stress causes small tears or micro-tears to the corpus cavernosum and corpus spongiosum tissue as well as blood vessels of the shaft 25 of the penis.

The second ring 14 also creates small tears in the tissue and blood vessels of the penis and isolates the blood flow between the first ring 13 and the second ring 14 of the penis. The second ring 14 can further prevent blood flow from returning to the body and further increases the amount of blood in the penis in order to cause the small tears created in the tissue and the blood vessels of the penis due to the pressure exerted onto the shaft of the penis by the first ring 13 and the second ring 14. The second ring 14 enables the blood to remain in the shaft of the penis in order to promote cell growth and cell division for the healing of the small tears in the penis.

Further, the rings 13, 14 cause pressure to be applied to the tissue and blood vessels in the penis and isolate the blood in the tissue of the penis therebetween. The user can further increase stress and pressure onto the tissue of the penis and blood vessels thereof by applying additional external pressure via pressing or squeezing the scrotum area. This external physical pressure causes small tears or micro-tears to form in the corpus cavernosum and corpus spongiosum tissue of the shaft 25 of the penis. The small tears cause the body to respond by increasing blood flow to the area in which the small tears are located in order to repair the tears.

The small tears caused by the pressure of the first ring 13 and the second ring 14 cause a physiologically process in the body of the user to repair the tears by increasing blood flow and red blood cells to the small tears in the tissue and blood vessel of the penis. As the blood flows to the small tears in the tissue and blood vessels of the penis, the tissue and blood vessels of the penis undergo cell growth known as hypertrophy and cell division known as hyperplasia. This physiological processes of hypertrophy and hyperplasia result in increasing both length and girth of the shaft 25 of the penis. The cell growth, division and tissue growth takes place during the recuperation period.

The penis enhancement apparatus 11 can be utilized every day, every other day, or as needed. The amount of time by which the penis enhancement apparatus 11 can be used may vary in correlation to the amount in which the user wishes to enlarge his penis. The penis enhancement apparatus 11 can be utilized in various increments being five, ten, fifteen, twenty, twenty-five minutes or more if desired or needed by the user. The penis enhancement apparatus 11 can be made in various sizes and colors in order to accommodate the needs of the user.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of enlarging the penis comprising the steps of:

provicing a first ring and a second ring, wherein each of said first ring and said second ring comprise an opening configured to receive a penis therethrough;

adjusting said opening of said first ring and said opening of said second ring to fit a penis;

placing said first ring near a tip of a shaft of said penis, wherein said placement of said first ring causes pressure to one or more tissues and blood vessels of the penis causing a plurality of small tears in said one or more tissues of said penis;

placing said second ring onto a base of said shaft of said penis, wherein said placement of said second ring causes a plurality of small tears in said one or more tissues and one or more blood vessels of said penis, said placement of said second ring isolating blood in said one or more tissues and said one or more blood vessels in said penis;

squeezing a scrotum to pump said blood of said penis into said shaft of said penis to cause said plurality of small tears in said one or more tissues of said penis and one or more blood vessels of said penis, said squeezing of said scrotum configured to induce physiological processes of cell growth and cell division in said one or more tissues of said penis and said one or more blood vessels of said penis causing an increase in a length and a girth of said penis.

* * * * *